United States Patent [19]

Tokuda et al.

[11] 4,269,857

[45] May 26, 1981

[54] CONTROL OF PLANT-VIRUS DISEASES

[75] Inventors: Takuro Tokuda; Susumu Ikeda; Yoshikazu Kubota; Tutomu Takagi; Yuuichi Kokagi, all of Iwaki, Japan

[73] Assignee: Kureha Kagaku Kogyo Kabushiki Kaisha, Tokyo, Japan

[21] Appl. No.: 86,441

[22] Filed: Oct. 19, 1979

[30] Foreign Application Priority Data

Nov. 2, 1978 [JP] Japan ................................ 53-135382

[51] Int. Cl.$^3$ ...................... A61K 31/13; A61K 31/70
[52] U.S. Cl. .................................... 424/325; 424/180; 424/343
[58] Field of Search .................... 536/22, 18; 424/180, 424/325, 343; 260/584 R

[56] References Cited

U.S. PATENT DOCUMENTS 3,313,682   4/1967   Zenitz .................................. 424/325

FOREIGN PATENT DOCUMENTS 4028484   7/1974   Japan .................................. 260/584 R

*Primary Examiner*—Johnnie R. Brown
*Assistant Examiner*—Blondel Hazel
*Attorney, Agent, or Firm*—Wegner & Bretschneider

[57] ABSTRACT

Disclosed herein control of plant-virus diseases by applying a compound obtained by reducing the reaction product of an n-alkylamine with a sugar or a salt thereof on the plant to be protected from the plant-virus as an active ingredient.

15 Claims, No Drawings

CONTROL OF PLANT-VIRUS DISEASES

BACKGROUND OF THE INVENTION

The present invention relates to control of plant-virus diseases by applying as an active ingredient a chemical compound represented by the general formula:

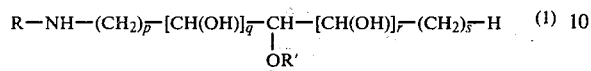   (1)

wherein R denotes an alkyl group having 3 to 18 carbon atomed; R' denotes a hydrogen atom or a glycopyranosyl group; p denotes an integer of one or 2; q denotes also one or 2, provided $p+q=3$; r denotes also one or 2; and s denotes 0 or one, provided $r+s=1$ or 2, or a salt thereof on the plant to be protected from the plant-virus.

Hitherto, various crops cultivated in fields and in various facilities, for instance, tobacco, tomato, cucumber, strawberry, Japanese radish, potato, Chinese cabbage, piment, etc. have been suffered a very large damage from plant viruses. Intensification of and reducing the man-power in agriculture are very critical in increasing the damage moreover. In spite of the strong demand of the breeding resistant varieties and the development of anti-virus agents, the situation is now quite unsatisfactory.

That is, the controlling of plant virus diseases has hitherto been carried out by pulling out the plants suffering from the disease or by controlling the vectors of plant viruses such as aphids, leafhoppers, planthoppers, nematodes. However, since these methods cannot positively control the plant virus diseases, the development of the agents effective in directly controlling the plant viruses themselves has been eagerly desired. As substances which are physiologically active against plant virus diseases, anti-metabolites such as 2-thiouracil, 5-fluorouracil, 8-azaquanine, etc., antibiotics such as blasticidin S, formycin B, aabomycin A, etc., polysaccharides and proteins produced by micro-organisms and polysaccharides, proteins and tannins derived from plants have been known. Of these substances, anti-metabolites and antibiotics have drawbacks such as giving phytotoxity to plants and having no persistency, and polysaccharides, proteins, tannins, etc. have defects of not inhibiting the infection of the viruses by vectors such as aphids.

The inventors, in considering the above-mentioned situations, have studied to find an effective compound against a wide variety of plant virus diseases such as cucumber mosaic virus disease, tobacco mosaic virus disease, etc., which is not phytotoxic to plant body and is safe to human and useful animals. As a result, the inventors have found that the compound shown as above in the formula (1) and its salt answer the above-mentioned purpose, and then completed the present invention.

Accordingly, the purpose of the present invention is to effectively control not only the plant-virus diseases infected by plant sap but also the plant-virus infected by vectors without giving any phytotoxic action on the plants to be protected from such plant virus diseases. The other purposes will become apparent in the ensuing specification and claims.

DETAILED DESCRIPTION OF THE INVENTION

The characteristic of the present invention resides in controlling the plant-virus diseases by applying as an active ingredient a chemical compound represented by the formula:

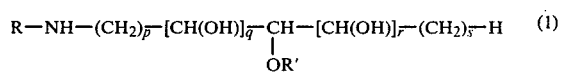   (1)

wherein R denotes an alkyl group having 3 to 18 carbon atoms; R' denotes a glycopyranosyl group; p denotes an integer of one or 2; q denotes an integer of also one or 2, provided $p+q=3$; r denotes an integer of one or 2 and s denotes an integer of 0 or one, provided $r+s=$ one or 2, or a salt thereof onto the plant to be protected from the plant-virus disease.

The compound represented by the above-mentioned general formula (1) is produced by at first bringing n-alkylamine into reaction with a sugar in a solvent and then reducing the reaction product.

Alkyl group of the alkylamine herein used is an alkyl group having 3 to 18 carbon atoms, and the sugar is a monosaccharide or disaccharide, the monosaccharide being preferably a pentose or a hexose. The salt of the above-mentioned compound of the general formula (1) is selected from the group consisting of the salts prepared from the compound represented by the formula (1) and an inorganic acid such as hydrochloric acid, hydrobromic acid, phosphoric acid, sulfuric acid and nitric acid and of the salts prepared from the compound represented by the formula (1) and an organic acid such as acetic acid, propionic acid, malic acid, citric acid, maleic acid, fumalic acid, succinic acid, glycolic acid, tartaric acid, benzoic acid, hydroxybenzoic acids (o-, m- and p-), cumaric acids (o-, m- and p-), protocathecuic acid, gallic acid, caffeic acid, nicotinic acid, shikimic acid, chlorogenic acid, quinic acid, ascorbic acid and mandelic acid.

The followings are instances of syntheses of the representative compounds of the general formula (1) and its salts:

EXAMPLE OF SYNTHESES 1

Hydrochloride of 1-deoxy-1-n-dodecylamino-D-glucitol.

A suspension of 18.0 g (0.1 mole) of D-glucose and 18.5 g (0.1 mole) of n-dodecylamine in 150 ml of methanol was heated under reflux for about 2 hours until glucose has completely dissolved in methanol, and after cooling to the room temperature, 7.6 g (0.2 mole) of sodium borohydride were added to the solution gradually with care not to cause bumping. After completing the addition of borohydride, the reaction was made complete by heating under reflux for 30 minutes. After evaporating the solvent from the reaction mixture, 50 ml of a 10% methanolic solution of hydrochloric acid was added to the residue and the methanol was evaporated off from the mixture in a rotary evaporator under reduced pressure. After repeating this procedure of de-boronation three times to remove the boron completely, the residue was suspended in methanol and the thus-crystallized-out common salt was filtered off. The crystals which deposited on condensing the filtrate were recrystallized from methanol to be colorless needle-like crystals of melting at 171° to 173° C. weighing 22.3 g (yield of 57.8% of theoretical).

Elementary analysis found: 55.8% of carbon, 10.4% of hydrogen, 3.5% of nitrogen and 9.8% of chlorine.

Calculated as $C_{18}H_{40}ClNO_5$: 56.01% of carbon, 10.45% of hydrogen, 3.63% of nitrogen and 9.18% of chlorine.

EXAMPLE OF SYNTHESES 2

1-Deoxy-1-n-dodecylamino-D-glucitol.

In an aqueous solution containing 7.7 g (0.02 mole) of the compound obtained by Example of syntheses 1 in 100 ml of water, 3 ml of an aqueous 30% solution of sodium hydroxide was added to obtaine deposited crystals. After collecting the crystals by filtration and washing them with water, the crystals were recrystallized from methanol to obtain colorless needle-like crystals melting at 128° to 130° C. in an amount of 6.3 g (yield of 90% of the theoretical).

An elementary analysis found: 60.7% of carbon, 11.0% of hydrogen and 4.0% of nitrogen.

Calculated as $C_{18}H_{39}NO_5$: 61.86% of carbon, 11.25% of hydrogen and 4.01% of nitrogen.

EXAMPLE OF SYNTHESES 3 p-Hydroxybenzoate of 1-deoxy-1-n-dodecylamino-D-mannitol.

One gram (2.9 millimole) of 1-deoxy-1-n-dodecylamino-D-mannitol and 0.4 g (2.9 millimole) of p-hydroxybenzoic acid were dissolved in 50 ml of methanol while heating the methanol. The thus deposited crystals were recrystallized from methanol to obtain colorless needle-like crystals melting at 171° to 173° C. in an amount of 1.1 g (yield of 78% of the theoretical).

An elementary analysis found: 60.8% of carbon, 9.1% of hydrogen and 2.7% of nitrogen.

Calculated as $C_{25}H_{45}NO_8$: 61.58% of carbon, 9.30% of hydrogen and 2.87% of nitrogen.

The followings are the representative concrete examples of the compounds of the present invention and each of the compounds is obtainable by the following method shown in the above-mentioned examples of syntheses. It is to be added that the compounds of the present invention are not restricted to the under-mentioned examples.

Compound (1)
1-Deoxy-1-n-propylamino-D-glucitol.

$HOH_2C-CH-CH-CH-CH-CH_2NH\ C_3H_7$,
    |    |    |    |
    OH   OH   OH   OH (with OH on 4th carbon from left as shown)

melting at 144 to 146° C.

Compound (2)
Hydrochloride of Compound (1).

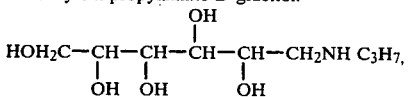

melting at 143 to 144° C.

Compound (3)
1-Deoxy-1-n-butylamino-D-glucitol.

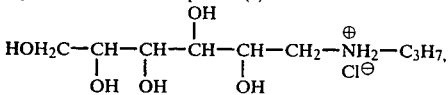

melting at 130 to 132° C.

Compound (4)
Hydrochloride of Compound (3):

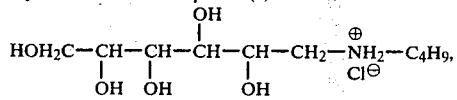

melting at 159 to 161° C.

Compound (5)
1-Doxy-1-n-pentylamino-D-glucitol.

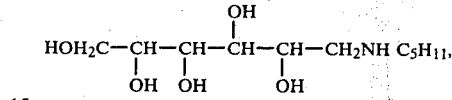

melting at 135 to 137° C.

Compound (6)
Hydrochloride of Compound (5).

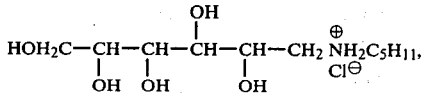

melting at 166 to 168° C.

Compound (7)
1-Deoxy-1-n-hexylamino-D-glucitol.

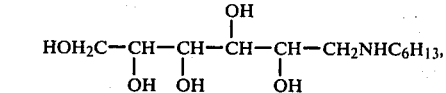

melting at 109 to 115° C.

Compound (8)
1-Deoxy-1-n-octylamino-D-glucitol.

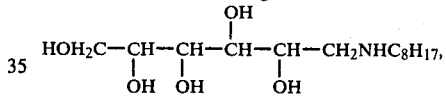

melting at 124 to 127° C.

Compound (9)
Hydrochloride of Compound (8).

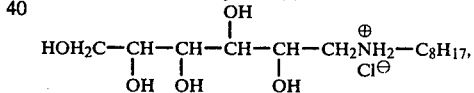

melting at 171 to 173° C.

Compound (10)
1-Deoxy-1-n-decylamino-D-glucitol.

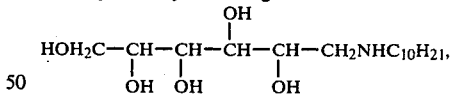

melting at 125 to 126° C.

Compound (11)
Hydrochloride of Compound 10.

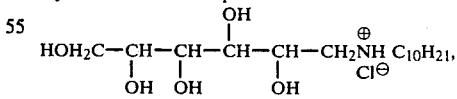

melting at 173 to 175° C.

Compound (12)
1-Deoxy-1-n-dodecylamino-D-glucitol.

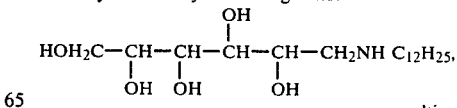

melting at 128 to 130° C.

Compound (13)
Hydrochloride of Compound (12).

-continued

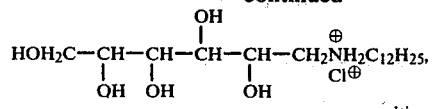

melting at 171 to 173° C.

Compound (14)
p-Hydroxybenzoate of Compound (12).

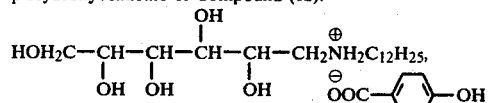

melting at 139 to 142° C.

Compound (15)
Gallate of Compound (12).

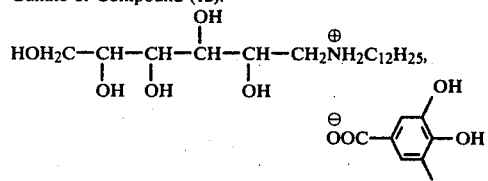

melting at 170° C.

Compound (16)
Salycilate of Compound (12).

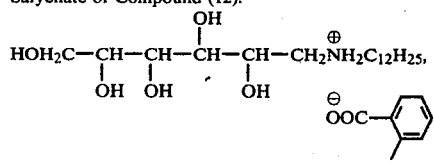

melting at 83 to 86° C.

Compound (17)
Caffeate of Compound (12).

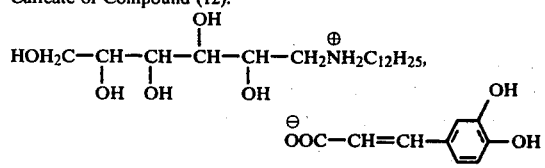

melting at 90 to 92° C.

Compound (18)
1-Deoxy-1-n-tetradecylamino-D-glucitol.

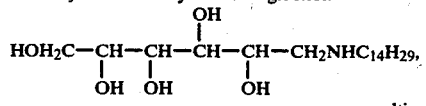

melting at 127 to 128° C.

Compound (19)
Hydrochloride of Compound (18).

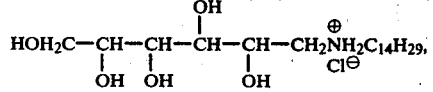

melting at 168 to 170° C.

Compound (20)
1-Deoxy-1-n-pentadecylamino-D-glucitol.

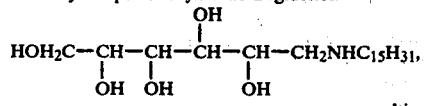

melting at 129 to 131° C.

Compound (21)
Hydrochloride of Compound (20).

-continued

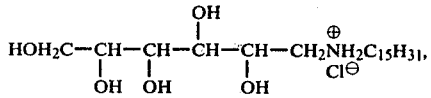

melting at 170 to 175° C.

Compound (22)
1-Deoxy-1-n-hexadecylamino-D-glucitol.

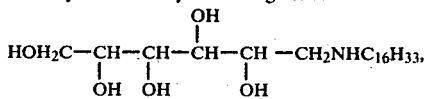

melting at 128 to 129° C.

Compound (23)
Hydrochloride of Compound (22).

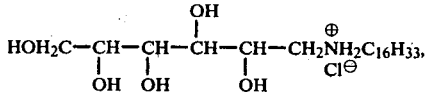

melting at 167 to 170° C.

Compound (24)
1-Deoxy-1-n-octadecylamino-D-glucitol.

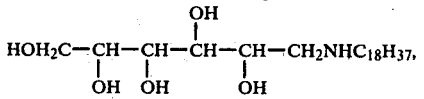

melting at 123 to 125° C.

Compound (25)
Hydrochloride of Compound (24).

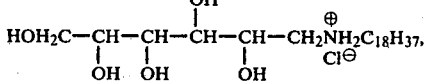

melting at 164 to 165° C.

Compound (26)
1-Deoxy-1-n-decylamino-D-mannitol.

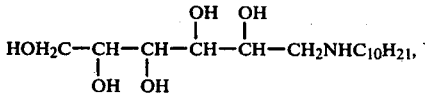

melting at 151 to 152° C.

Compound (27)
Hydrochloride of Compound (26).

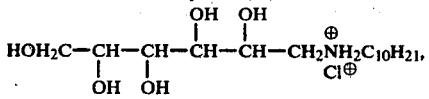

melting at 182 to 184° C.

Compound (28)
1-Deoxy-1-n-dodecylamino-D-mannitol.

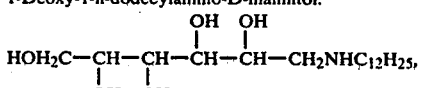

melting at 146 to 147° C.

Compound (29)
Hydrochloride of Compound (28).

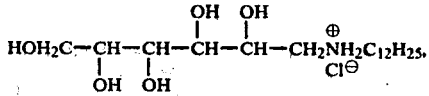

melting at 180 to 181° C.

Compound (30)
p-Hydroxybenzoate of Compound (28):

-continued

HOH$_2$C—CH—CH—CH—CH—CH$_2$NH$_2$C$_{12}$H$_{15}$,
$\quad\quad\quad$|$\quad$|$\quad\quad$|$\quad$|
$\quad\quad\quad$OH OH$\quad$OH OH $^-$OOC—⟨benzene⟩—OH melting at 172 to 173° C.

Compound (31)
Gallate of Compound (28).

HOH$_2$C—CH—CH—CH—CH—CH$_2$NH$_2$C$_{12}$H$_{25}$,
$\quad\quad\quad$|$\quad$|$\quad\quad$|$\quad$|
$\quad\quad\quad$OH OH$\quad$OH OH $^-$OOC—⟨benzene⟩—(OH)$_3$ melting at 170 to 171° C.

Compound (32)
Caffeate of Compound (28).

HOH$_2$C—CH—CH—CH—CH—CH$_2$NH$_2$C$_{12}$H$_{25}$,
$\quad\quad\quad$|$\quad$|$\quad\quad$|$\quad$|
$\quad\quad\quad$OH OH$\quad$OH OH $^-$OOC—⟨benzene⟩—(OH)$_2$ melting at 77 to 78° C.

Compound (33)
1-Deoxy-1-n-tetradecylamino-D-mannitol.

HOH$_2$C—CH—CH—CH—CH—CH$_2$NHC$_{14}$H$_{29}$,
$\quad\quad\quad$|$\quad$|$\quad\quad$|$\quad$|
$\quad\quad\quad$OH OH$\quad$OH OH melting at 144 to 145° C.

Compound (34)
Hydrochloride of Compound (33).

HOH$_2$C—CH—CH—CH—CH—CH$_2$NH$_2$C$_{14}$H$_{29}$, Cl$^-$
$\quad\quad\quad$|$\quad$|$\quad\quad$|$\quad$|
$\quad\quad\quad$OH OH$\quad$OH OH melting at 175 to 178° C.

Compound (35)
1-Deoxy-1-n-dodecylamino-D-galactitol.

HOH$_2$C—CH—CH—CH—CH—CH$_2$NHC$_{12}$H$_{25}$,
$\quad\quad\quad$|$\quad$|$\quad\quad$|$\quad$|
$\quad\quad\quad$OH OH$\quad$OH OH melting at 150 to 151° C.

Compound (36)
Hydrochloride of Compound (35).

HOH$_2$C—CH—CH—CH—CH—CH$_2$NH$_2$C$_{12}$H$_{25}$, Cl$^-$
$\quad\quad\quad$|$\quad$|$\quad\quad$|$\quad$|
$\quad\quad\quad$OH OH$\quad$OH OH melting at 220 to 221° C.

Compound (37)
p-Hydroxybenzoate of Compound (35).

HOH$_2$C—CH—CH—CH—CH—CH$_2$NH$_2$C$_{12}$H$_{25}$,
$\quad\quad\quad$|$\quad$|$\quad\quad$|$\quad$|
$\quad\quad\quad$OH OH$\quad$OH OH $^-$OOC—⟨benzene⟩—OH melting at 180 to 181° C.

Compound (38)
1-Deoxy-1-n-dodecylamino-L-rhamnitol.

-continued

H$_3$C—CH—CH—CH—CH—CH$_2$NHC$_{12}$H$_{25}$,
$\quad\quad$|$\quad$|$\quad\quad$|$\quad$|
$\quad\quad$OH OH$\quad$OH OH melting at 130 to 131° C.

Compound (39)
Hydrochloride of Compound (38).

H$_3$C—CH—CH—CH—CH—CH$_2$NH$_2$C$_{12}$H$_{25}$, Cl$^-$
$\quad\quad$|$\quad$|$\quad\quad$|$\quad$|
$\quad\quad$OH OH$\quad$OH OH melting at 189 to 190° C.

Compound (40)
p-Hydroxybenzoate of Compound (38).

H$_3$C—CH—CH—CH—CH—CH$_2$NH$_2$C$_{12}$H$_{25}$,
$\quad\quad$|$\quad$|$\quad\quad$|$\quad$|
$\quad\quad$OH OH$\quad$OH OH $^-$OOC—⟨benzene⟩—OH melting at 168 to 169° C.

Compound (41)
1,2-Dideoxy-1-n-dodecylamino-D-glucitol.

HOH$_2$C—CH—CH—CH—CH$_2$—CH$_2$NHC$_{12}$H$_{25}$,
$\quad\quad\quad$|$\quad$|$\quad\quad$|
$\quad\quad\quad$OH OH$\quad$OH melting at 112 to 114° C.

Compound (42)
Hydrochloride of Compound (41).

HOH$_2$C—CH—CH—CH—CH$_2$—CH$_2$NH$_2$C$_{12}$H$_{25}$, Cl$^-$
$\quad\quad\quad$|$\quad$|$\quad\quad$|
$\quad\quad\quad$OH OH$\quad$OH melting at 189 to 191° C.

Compound (43)
1-Deoxyl-1-n-decylamino-D-ribitol.

HOH$_2$C—CH—CH—CH—CH$_2$NHC$_{10}$H$_{21}$,
$\quad\quad\quad$|$\quad$|$\quad$|
$\quad\quad\quad$OH OH OH melting at 177° C.

Compound (44)
1-Deoxy-1-n-dodecylamino-D-ribitol.

HOH$_2$C—CH—CH—CH—CH$_2$NHC$_{12}$H$_{25}$,
$\quad\quad\quad$|$\quad$|$\quad$|
$\quad\quad\quad$OH OH OH melting at 77 to 79° C.

Compound (45)
p-Hydroxybenzoate of Compound (44).

HOH$_2$C—CH—CH—CH—CH$_2$NH$_2$C$_{12}$H$_{25}$,
$\quad\quad\quad$|$\quad$|$\quad$|
$\quad\quad\quad$OH OH OH $^-$OOC—⟨benzene⟩—OH melting at 131 to C.

Compound (46)
Hydrochloride of Compound (44).

HOH$_2$C—CH—CH—CH—CH$_2$NH$_2$C$_{12}$H$_{25}$, Cl$^-$
$\quad\quad\quad$|$\quad$|$\quad$|
$\quad\quad\quad$OH OH OH melting at 95 to 100° C.

Compound (47)
Gallate of Compound (44).

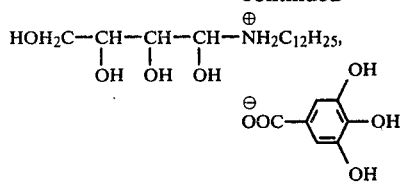

melting at 117 to 120° C.

Compound (48)
Caffeate of Compound (44).

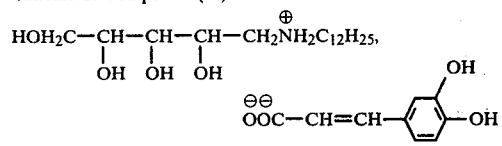

melting at 30 to 35° C.

Compound (49)
Hydrochloride of 1-deoxy-1-n-tetradecylamino-D-ribitol.

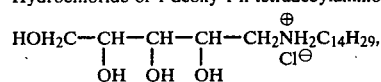

melting at 135 to 137° C.

1 Compound (50):
1-Deoxy-1-n-decylamino-D-xylitol.

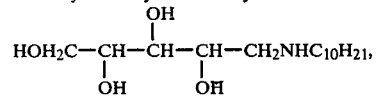

melting at 83 to 85° C.

Compound (51)
Hydrochloride of Compound (50).

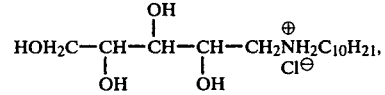

melting at 127 to 130° C.

Compound (52)
1-Deoxy-1-n-dodecylamino-D-xylitol.

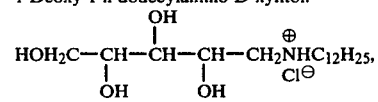

melting at 80 to 85° C.

Compound (53)
1-Deoxy-1-n-tetradecylamino-D-xylitol.

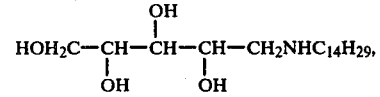

melting at 83 to 84° C.

Compound (54)
Hydrochloride of Compound (53).

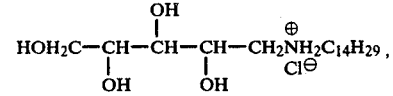

melting at 80 to 83° C.

Compound (55)
1,2-dideoxy-1-n-dodecylamino-D-ribitol.

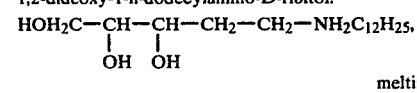

melting at 109 to 115° C.

Compound (56)
1-Deoxy-1-n-octadecylamino-maltitol.

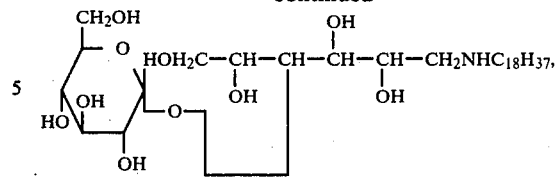

melting at 89 to 94° C.

Compound (57)
Hydrochloride of Compound (56).

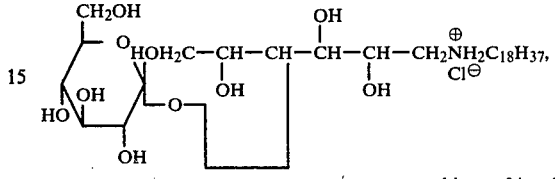

melting at 94 to 96° C.

Compound (58)
1-Deoxy-1-n-dodecylaminolactitol.

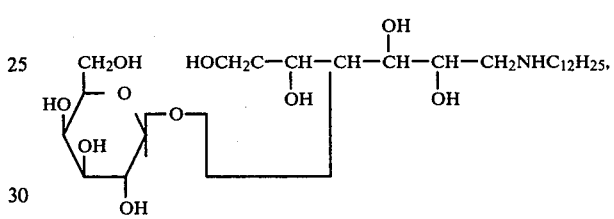

melting at 115 to 118° C.

Compound (59)
1-Deoxy-1-n-octadecylaminolactitol.

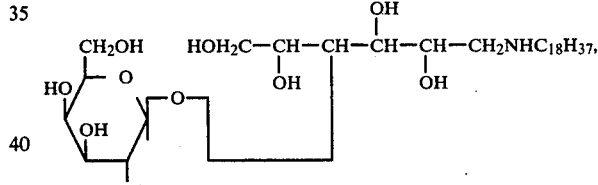

melting at 74 to 79° C.

Compound (60)
Hydrochloride of Compound (59).

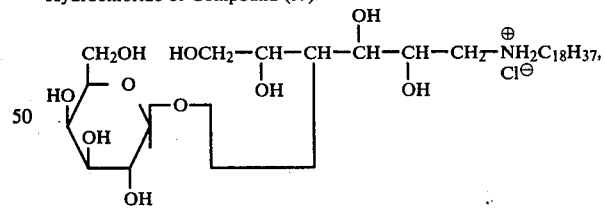

melting at 117 to 119° C.

Compound (61)
1-Deoxy-1-n-dodecylaminocellobitol.

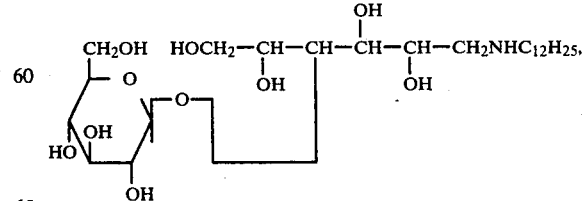

melting at 134 to 136° C.

Compound (62)
1-Deoxy-1-n-octadecylaminocellobitol.

-continued

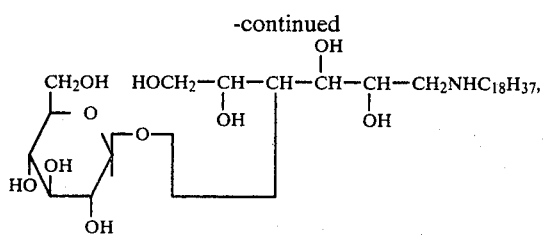

melting at 129 to 134° C.

Compound (63)

Hydrochloride of Compound (62).

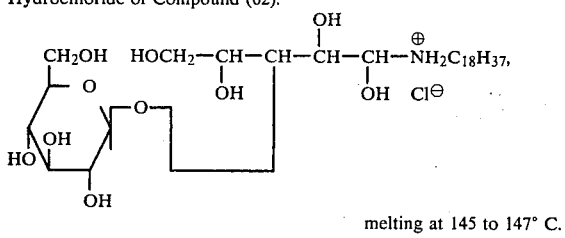

melting at 145 to 147° C.

On the actual application of the compound of the present invention for the control of plant virus, the compound can be used as it is without adding any other components, and it can be formulated to be a formulation (composition) such as wettable powders, dusts, emulsive concentrates, granules, liquids, oil solutions, etc. by admixing pertinent carrier, diluent, extender, or other adjuvant. In some cases, it may be admixed with other pesticides, fertilizers, etc.

The followings are Examples of the compositions for controlling plant virus containing the compound of the present invention as an active ingredient.

In addition, it goes without saying that the kinds and the ratios of mixing of adjuvants to the compound of the present invention are possibly varied in a wide range.

EXAMPLE 1

Wettable powder.

Twenty parts by weight of 1-deoxy-1-n-octadecylamino-D-glucitol (Compound 24), 2 parts by weight of an emulsifier of polyethylenealkylphenyl ether and 78 parts by weight of diatomaceous earth were mixed and pulverized to be a wettable powder. The thus formulated composition is applied after suspending into water.

EXAMPLE 2

Dust.

Five parts by weight of 1-deoxy-1-n-dodecylamino-D-mannitol hydrochloride (Compound 29) and 95 parts by weight of clay were uniformly mixed and pulverized to be a dust formulation. The thus formulated composition is applied as it is.

EXAMPLE 3

Liquid (Solution).

Ten parts by weight of 1-deoxy-1-n-deodecylamino-D-glucitol, 88 parts by weight of ethyleneglycol monobutylether and 2 parts by weight of an emulsifier of polyethylenealkylphenyl ether were mixed well to prepare a solution (so-called a liquid formulation). The thus prepared composition is applied after diluting with water.

The followings are the test results of the compounds of the present invention in the plant virus disease-controlling experiments. In the experiments one of the compounds of the present invention was formulated as in the above-mentioned Example 3 and after diluting the formulated composition with water to a predetermined concentration.

TEST RESULT 1

In this test, the inhibiting action of the compound of the present invention against the formation of local lesion due to the infection of tobacco mosaic virus (TMV) was examined by the half-leaf method using primary leaves of kedny been plants (variety: Otebo). TMV was inoculated on the primary leaf of kedney been plant, and just after the inoculation, the diluted liquid of the compound was painted on the half surface of the leaf and water was painted on the other half surface of the leaf. The concentration of the compounds of the present invention in the liquid was 500 ppm, and the inoculum was adjusted to form about 50 topical lesion spots on the half surface of the leaf painted with water (control). Ten leaves were usually used for the evaluation of one compound, and the rate of inhibition of lesion spot formation was derived from the following formula:

$$\text{Rate of inhibition} = \left(1 - \frac{\text{total number of spots on compound-treated leaves}}{\text{total number of spots on water-treated leaves}}\right) \times 100\ (\%)$$

The thus obtained rates of inhibition were evaluated according to the following criteria:

| Rate of inhibition (%) | Evaluated Remarks |
|---|---|
| 100–90 | A |
| 90–70 | B |
| 70–50 | C |
| 50–30 | D |
| less than 30 | E |

The results of the examination are shown in Table 1. Each compound is represented by its number as shown in Examples.

TABLE 1

Results of Evaluation of the Compounds of the Present Invention in TMV- controlling test.

| No. of Compounds | Evaluation | No. of Compounds | Evaluation | No. of Compounds | Evaluation |
|---|---|---|---|---|---|
| 1 | B | 23 | B | 45 | B |
| 2 | B | 24 | A | 46 | A |
| 3 | B | 25 | A | 47 | A |
| 4 | B | 26 | A | 48 | A |
| 5 | B | 27 | A | 49 | A |
| 6 | B | 28 | A | 50 | B |
| 7 | B | 29 | A | 51 | A |
| 8 | B | 30 | B | 52 | A |
| 9 | B | 31 | A | 53 | A |
| 10 | A | 32 | A | 54 | A |
| 11 | A | 33 | B | 55 | A |
| 12 | A | 34 | B | 56 | A |
| 13 | A | 35 | B | 57 | B |
| 14 | A | 36 | B | 58 | A |
| 15 | A | 37 | B | 59 | A |
| 16 | A | 38 | B | 60 | B |
| 17 | B | 39 | B | 61 | A |
| 18 | B | 40 | B | 62 | B |
| 19 | B | 41 | A | 63 | B |
| 20 | B | 42 | B | Water | E |
| 21 | B | 43 | A | | |
| 22 | B | 44 | B | | |

TEST RESULTS 2

The compounds evaluated as A in Test results 1 were further tested of their inhibiting activity against the disease causing infection due to cucumber mosaic virus (CMV) on leaves of 10 tobacco plant after 2 month's growing from sowing, tobacco plant being the variety of KY-57. The inoculum was a 100 times-diluted liquid of a sap of infected and suffered leaves of tobacco from CMV and it was inoculated by carborumdum method on the developed leaves of the tobacco plant. Just after the inoculation, each diluted liquid containing a compound to be tested at a concentration of 500 ppm was sprayed on the inoculated tobacco plants at a rate of 10 ml per plant. As control, water was sprayed. The occurrence of the disease was investigated after 10 days of the inoculation counting the number of plants without occurence of the disease per number of plants tested. The results were evaluated according to the following criterion:

| Number of plants without occurrence of disease/10 plants | Evaluation |
|---|---|
| 10/10–8/10 | A |
| 7/10–5/10 | B |
| 4/10–2/10 | C |
| less than 1/10 | D |

The results of Test results 2 are shown in Table 2.

TABLE 2

| No. of Compound | Evaluation | No. of Compound | Evaluation | No. of Compound | Evaluation |
|---|---|---|---|---|---|
| 10 | A | 25 | A | 43 | B |
| 11 | A | 26 | A | 46 | B |
| 12 | A | 27 | A | 47 | B |
| 13 | A | 28 | B | 48 | A |
| 14 | A | 29 | A | 49 | A |
| 15 | A | 31 | B | 51 | B |
| 16 | A | 32 | B | 52 | A |
| 24 | A | 41 | B | 53 | A |
| 54 | B | 58 | A | Water | D |
| 55 | A | 59 | B | | |
| 56 | B | 61 | A | | |

TEST RESULTS 3

The compounds evaluated as A in Test results 2 were further tested as follows:

The cucumber plants growing for two weeks after sowing in greenhouse were sprayed by each liquid containing each compound at a concentration of 500 ppm (variety of cucumber: Kinseisanto). After drying at room temperature about 3 hours, wingless aphids (*Myzus persicae*, Sulzer) which had been put on the suffered cucumber plant from CMV and shipped the plant sap containing CMV were transmigrated to the sprayed cucumber plants at a rate of 5 insects per plant. On the next day of the transmigration, the insects were killed by spraying dichlorvos in the plants. After one week of the spray of the compound of the present invention, the effectiveness of the compound in inhibiting the occurrence of the sign of disease due to the virus was investigated as the number of plants without the sign of disease per number of plants sprayed. As the control, water was sprayed.

The results are shown in Table 3.

TABLE 3

Test Results against CMV on Cucumber Plants

| No. of Compound | Evaluation | No. of Compound | Evaluation |
|---|---|---|---|
| 10 | B | 27 | B |
| 11 | B | 29 | B |
| 12 | A | 48 | A |
| 13 | A | 49 | A |
| 14 | B | 52 | A |
| 15 | A | 53 | A |
| 16 | A | 55 | A |
| 24 | A | 58 | B |
| 25 | A | 61 | B |
| 26 | B | Water | D |

What we claim is:

1. A method of controlling a plant virus disease occurring on a plant which comprises applying an effective amount of a chemical compound represented by the formula:

$$R-NH-(CH_2)_p-(CHOH)_n-CH_2OH$$

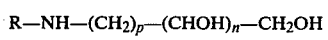

wherein R is n-alkyl group having 10 to 18 carbon atoms, p represents an integer of one or two and n represents an integer of three or four, provided p+n equals four or five, or of a salt thereof onto the plant to be protected from the plant virus disease.

2. The method according to claim 1 wherein the salt thereof is a salt of an inorganic acid.

3. The method according to claim 1 wherein the salt thereof is a salt of an organic acid.

4. A composition for controlling a plant virus disease comprising an effective amount of at least one substance selected from the group consisting of compounds having the formula:

$$R-NH-(CH_2)_p-(CHOH)_n-CH_2OH$$

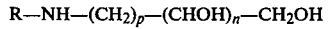

wherein R is n-alkyl group having 10 to 18 carbon atoms, p represents an integer of one or two and n represents an integer of three or four, provided p+n equals four or five, and salts thereof, and at least one member selected from the group consisting of carriers, diluents, spreaders and other adjuvants which are applicable to an agricultural chemical.

5. The composition according to claim 4 wherein said substance is 1-deoxy-1-n-deodecylamino-D-glucitol.

6. The composition according to claim 4 wherein said substance is 1-deoxy-1-n-dodecylamino-D-glucitol hydrochloride.

7. The composition according to claim 4 wherein said substance is 1-deoxy-1-n-dodecylamino-D-glucitol gallate.

8. The composition according to claim 4 wherein said substance is 1-deoxy-1-n-dodecylamino-D-glucitol salicylate.

9. The composition according to claim 4 wherein said substance is 1-deoxy-1-n-octadecylamino-D-glucitol.

10. The composition according to claim 4 wherein said substance is 1-deoxyl-n-octadecylamino-D-glucitol hydrochloride.

11. The composition according to claim 4 wherein said substance is 1-deoxy-1-n-dodecylamino-D-ribitol caffeate.

12. The composition according to claim 4 wherein said substance is 1-deoxy-1-n-tetradecylamino-D-ribitol hydrochloride.

13. The composition according to claim 4 wherein said substance is 1-deoxy-1-n-dodecylamino-D-xylitol.

14. The composition according to claim 4 wherein said substance is 1-deoxy-1-n-tetradecylamino-D-xylitol.

15. The composition according to claim 4 wherein said substance is 1,2-dideoxyl-1-n-dodecylamino-D-ribitol.

* * * * *